(12) United States Patent
Phillips et al.

(10) Patent No.: US 9,840,904 B2
(45) Date of Patent: Dec. 12, 2017

(54) MONITORING HYDROCARBON FLUID FLOW

(71) Applicant: Vetco Gray Controls Limited, Nailsea, Bristol (GB)

(72) Inventors: Raymond Phillips, Nailsea (GB); Nicholas Josep Ellson, Nailsea (GB)

(73) Assignee: Vetco Gray Controls Limited, Nailsea (GB)

( * ) Notice: Subject to any disclaimer, the term of this patent is extended or adjusted under 35 U.S.C. 154(b) by 0 days.

(21) Appl. No.: 15/227,457

(22) Filed: Aug. 3, 2016

(65) Prior Publication Data

US 2016/0341029 A1    Nov. 24, 2016

Related U.S. Application Data

(63) Continuation-in-part of application No. 13/469,898, filed on May 11, 2012, now Pat. No. 9,435,189.

(51) Int. Cl.

| | |
|---|---|
| *E21B 47/00* | (2012.01) |
| *E21B 47/06* | (2012.01) |
| *E21B 34/04* | (2006.01) |
| *G01F 1/74* | (2006.01) |
| *E21B 33/035* | (2006.01) |
| *G01N 33/28* | (2006.01) |

(52) U.S. Cl.
CPC ............ *E21B 47/0001* (2013.01); *G01F 1/74* (2013.01); *G01N 33/2823* (2013.01)

(58) Field of Classification Search
CPC .... E21B 47/0001; E21B 33/035; E21B 34/04; E21B 47/06; E21B 47/065
See application file for complete search history.

(56) References Cited

U.S. PATENT DOCUMENTS 4,289,020 A * 9/1981 Paap .................. G01N 33/2823
                                                            250/301
5,259,239 A * 11/1993 Gaisford .................. G01F 1/74
                                                            73/61.44
5,287,752 A * 2/1994 Den Boer ................. G01F 1/64
                                                            73/861.04

(Continued)

FOREIGN PATENT DOCUMENTS

| WO | 9615427 A1 | 5/1996 |
| WO | 2012000645 A1 | 1/2012 |

OTHER PUBLICATIONS

PCT Search Report and Written Opinion issued in connection with corresponding PCT Application No. PCT/US2017/069178 on Sep. 8, 2017.

*Primary Examiner* — James G Sayre
(74) *Attorney, Agent, or Firm* — GE Global Patent Operation

(57) ABSTRACT

A christmas tree assembly for a subsea hydrocarbon extraction facility, the christmas tree assembly includes a fluid pipeline and a sensor assembly comprising a plurality of sensors configured to monitor a plurality of properties relating to hydrocarbon fluid flow through the fluid pipeline. The sensor assembly includes a differential pressure sensor that is disposed at one or more of across a choke, around a bend or restriction in the pipeline or a dedicated flow restrictor integrated within the pipeline, and a bulk density sensor that is disposed in one or more of a blind T, before or after a choke or in an upwards section of the flow pipeline.

21 Claims, 6 Drawing Sheets

(56) References Cited

U.S. PATENT DOCUMENTS

| | | | |
|---|---|---|---|
| 2008/0319685 A1* | 12/2008 | Xie | G01N 22/00 702/45 |
| 2009/0114038 A1* | 5/2009 | Atkinson | G01F 1/44 73/861.63 |
| 2009/0277644 A1* | 11/2009 | Mcstay | E21B 33/035 166/336 |
| 2012/0111571 A1* | 5/2012 | Eriksen | B01D 17/06 166/336 |
| 2015/0368999 A1 | 12/2015 | Massa De Campos et al. | |

* cited by examiner

MONITORING HYDROCARBON FLUID FLOW

CROSS-REFERENCE TO RELATED APPLICATIONS

This Continuation-in-Part application claims the benefit of and priority to U.S. patent application Ser. No. 13/469,898 filed on 11 May 2012, status pending, the disclosure of which is incorporated herein by reference in its entirety.

TECHNICAL FIELD

The aspects of the disclosed embodiments relate to monitoring hydrocarbon fluid flow and in particular, monitoring hydrocarbon fluid flow at a christmas tree assembly of a subsea hydrocarbon extraction facility.

Hydrocarbon fluid flowing from an offshore oil reservoir or well is multiphase in nature in that it contains oil, gas and water and can also contain particulates such as sand. Multiphase meters are used to measure the content of gas, oil and water in the fluid, and other sensors are incorporated to measure the particulates. The sensor equipment is normally mounted on a christmas tree assembly, also referred to as a christmas tree, installed on the seabed, and is usually placed on the christmas tree assembly after the design has been established. Therefore, the sensor location is often dictated by practical issues rather than the optimum positions for measurements. For example, the current practice is to install a multiphase meter on the christmas tree with a sensor package positioned at a convenient position with respect to the christmas tree.

The sensor package usually contains a bundle of sensors. Because the sensors are bundled, the individual sensors may not all be ideally positioned to accurately measure their particular parameter. Some fluid flow measurement techniques require the flow to be conditioned (for example, laminar or turbulent) to be at their optimal accuracy. There is a need for a more accurate system and method of measurement of parameters in a christmas tree assembly.

Accordingly, it would be desirable to provide a sensor assembly arrangement for a christmas tree of subsea hydrocarbon extraction facility that addresses at least some of the problems identified above.

SUMMARY

The aspects of the disclosed embodiments are directed to a sensor assembly for a christmas tree in a subsea hydrocarbon extraction facility. Further advantageous modifications can be found in the dependent claims.

According to a first aspect, the disclosed embodiments are directed to a christmas tree assembly for a subsea hydrocarbon extraction facility. The christmas tree assembly includes a fluid pipeline and a sensor assembly comprising a plurality of sensors configured to monitor a plurality of properties relating to hydrocarbon fluid flow through the fluid pipeline. The sensor assembly includes a differential pressure sensor that is disposed at or across one or more of a choke, around a bend or restriction in the pipeline or a dedicated flow restrictor integrated within the pipeline; and a bulk density sensor that is disposed in one or more of a blind T, before or after a choke or in an upwards section of the flow pipeline. The combination of differential pressure measurement with the Bulk density can be used to provide a crude estimate of bulk flow rate.

In one embodiment, the density sensor is one or more of a torsional densitometer, an ultrasonic based density sensor or a gamma based density sensor.

In one embodiment the bulk density sensor is disposed proximate to an output of a control valve in the flow pipeline.

In one embodiment bulk density sensor is disposed in a straight portion of the flow pipeline between two sharp bends.

In one embodiment the sensor assembly comprises a temperature sensor and a pressure sensor, the temperature sensor and pressure sensor being disposed in a proximity of the bulk density sensor.

In one embodiment the temperature sensor and the pressure sensor are disposed in an insulated region of the flow pipeline in the proximity of the bulk density sensor.

In one embodiment the temperature sensor and the pressure sensor are disposed in a straight portion of the flow pipeline between two sharp bends.

In one embodiment the sensor assembly further comprises a gas void fraction sensor disposed in a flow region of the flow pipeline.

In one embodiment the flow region is a horizontal flow region.

In one embodiment the flow pipeline comprises a choke valve in a portion of the flow pipeline between a sharp bend and an exit of the flow pipeline, a bypass line disposed around the choke valve, and the gas void fraction sensor disposed in the bypass line.

In one embodiment the gas void fraction sensor comprises one or more of a ultrasound measurement device and a nuclear magnetic resonance device In one embodiment the gas void fraction sensor is disposed in a vertical flow region of the flow pipeline.

In one embodiment the gas void fraction sensor comprises one or more of an electrical impedance spectroscopy device, a microwave device and a gamma densitometer.

In one embodiment the sensor assembly comprises a temperature sensor, a pressure sensor and a water cut meter, the temperature sensor and pressure sensor being disposed in a proximity of the bulk density sensor.

In one embodiment the water cut meter comprises a local measurement close to the pipe wall in a high velocity area of the flow pipeline before a choke.

In one embodiment the water cut meter is an infrared absorption or torsional densitometer sensor configured to measure liquid toward a center of the flow pipeline in a well mixed flow. To avoid erosion of the device, it is preferable to put the device in a region of low velocity, such as after a blind T but before the choke, or alternatively, after the choke.

In one embodiment the water cut meter is disposed in a liquid dominant flow area of the flow pipeline.

In one embodiment the water cut meter is disposed in a blind T portion of the flow pipeline.

In one embodiment the sensor assembly further comprises a fluid velocity sensor disposed in a well-mixed, developed flow region of the fluid pipeline.

In one embodiment the sensor assembly further comprises one or more of a microwave cross correlation sensor, an electrical impedance cross correlation sensor or an NMR cross correlation sensor, ultrasound Doppler sensor disposed in a straight vertical, upwards flow section of the pipeline.

In one embodiment the sensor assembly further comprises an ultrasound Doppler sensor disposed after a choke or blind T in the flow pipeline.

Any one or more of the above embodiments can be combined together. These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following, the invention will be explained in more detail with reference to the example embodiments shown in the drawings, in which.

DETAILED DESCRIPTION OF THE DISCLOSED EMBODIMENTS

Figure 1:
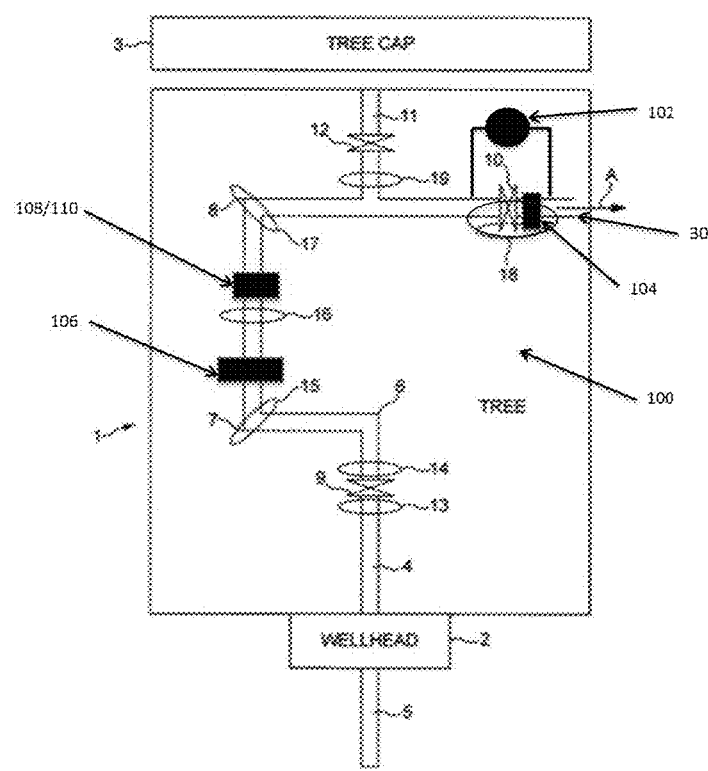
FIG. 1 is a schematic illustration of one example of a subsea christmas tree according to the disclosed embodiments.

FIG. 1 illustrates a schematic diagram of an exemplary sensor configuration 100 for a christmas tree assembly 1 of a subsea hydrocarbon extraction facility incorporating aspects of the disclosed embodiments. The aspects of the disclosed embodiments are directed to flow metering and distributed measurements around the christmas tree assembly.

FIG. 1 is a simplified schematic illustration of an exemplary christmas tree assembly 1 for a subsea hydrocarbon extraction facility incorporating aspects of the disclosed embodiments. In the example of FIG. 1, the Christmas tree assembly 1 illustrates the main hydrocarbon flow pipeline components and positions for installing sensors in accordance with the aspects of the disclosed embodiments.

In the example of FIG. 1, the subsea christmas tree assembly 1 is disposed between a wellhead 2 and a tree cap 3, in a manner as is generally understood. A flow or fluid pipeline 4 is fed from an oil or gas well production tubing 5 situated below the wellhead. The flow pipeline 4 is generally implemented either with a pipe to contain the hydrocarbon fluids which are under great pressure, or with drilled passage ways through large machined or forged metal blocks. The flow pipeline 4 exits the christmas tree assembly 1 to a flow line in the direction of arrow A at exit 30.

The physical configuration of the mechanical structure of the christmas tree assembly 1 includes several changes of direction for the hydrocarbon fluid by means of sharp bends in the flow pipeline 4. In the example of FIG. 1, the flow pipeline 4 includes a first sharp bend 6, a second sharp bend 7 and a third sharp bend 8. A sharp bend is generally defined as a change in direction in the pipeline in a range of approximately 45 degrees to and including approximately 90 degrees. Unlike curved or bent tubing where the radius of curvature follows the bend, in a sharp bend the radius changes for different points along the bend. Unlike a gradual bend, a sharp bend will disrupt and/or mix the flow of fluid. As will be described further below, the first sharp bend 6, the second sharp bend 7 and the third sharp bend 8 can provide optimized positions to locate sensors for flow metering and monitoring.

A flow control valve 9 is disposed in the pipeline 4 between the wellhead 2 and the first sharp bend 6. A choke valve 10 is disposed between the third sharp bend 8 and the exit 30 of the flow pipeline 4. A pipeline branch section 11 is disposed between the third sharp bend 8 and the choke 10. In one embodiment, the pipeline branch section 11 can be used to allow hydrocarbon fluids to exit the christmas tree assembly 1 in a different direction. A flow isolation valve 12 is disposed in the branch section 11.

The aspects of the disclosed embodiments utilize the knowledge of the flow regimes in the hydrocarbon flow pipeline 4 and valve configurations on the christmas tree assembly 1 to place suitable discrete sensors in the most appropriate positions to acquire a more accurate overall monitoring of properties relating to hydrocarbon fluid flow. In particular, the sensor assembly 100 of the disclosed embodiments provides improved flow metering and monitoring. The particular arrangement of sensors of the sensor assembly 100 utilizes the physical configuration of the christmas tree assembly 1 and the configuration of the flow pipeline 4 to enable measurements of such properties to be made by using discrete sensors each placed at or near an optimum position in the fluid flow for its measurement in the most meaningful manner.

The sensor assembly 100 shown in FIG. 1 includes at least a differential pressure sensor (dP) 102 and a first bulk density sensor 104. The aspects of the disclosed embodiments use the knowledge of the geometry of the christmas tree 1 together with the combination of the differential pressure sensor 102 and first bulk density sensor 104 to provide an estimate of the bulk flow rate in the christmas tree assembly 1.

The differential pressure sensor 102 is configured to be disposed across one or more of a choke, around a bend or restriction in the pipeline or a dedicated pressure drop device. The pressure drop device can comprises a Venturi, Orifice plate, V-cone or other pressure drop device. In one embodiment, the differential pressure sensor 102 is integrated in a vertical position in a well-mixed flow region within the pipeline 4. In alternate embodiments, any suitable orientation of the differential pressure sensor 102 can be realized. A well-mixed flow area can provide independent phase velocities through the use of industry recognized correlations/models. In the example of FIG. 1, the differential pressure sensor 102 is disposed across the choke valve 10. In an alternate embodiment, the differential pressure sensor 102 can be located in any suitable well mixed flow area of the christmas tree 1 where a pressure drop exists, such as after a or across a blind T or dedicated pressure drop device (Venturi, orifice plate, v-cone).

The first bulk density sensor 104 is configured to be disposed in one or more of a blind T, before or after a choke or in an upwards section of the flow pipeline. The exact location can depend on the specific type of bulk density sensor used. In the example shown in FIG. 1, the first bulk density sensor 104 is disposed between the choke valve 10 and the exit 30 of the flow pipeline 4. The first bulk density sensor 104 described herein can include one or more of a torsional densitometer, an ultrasonic (UT) based density sensor and a gamma based density sensor.

Figure 5:
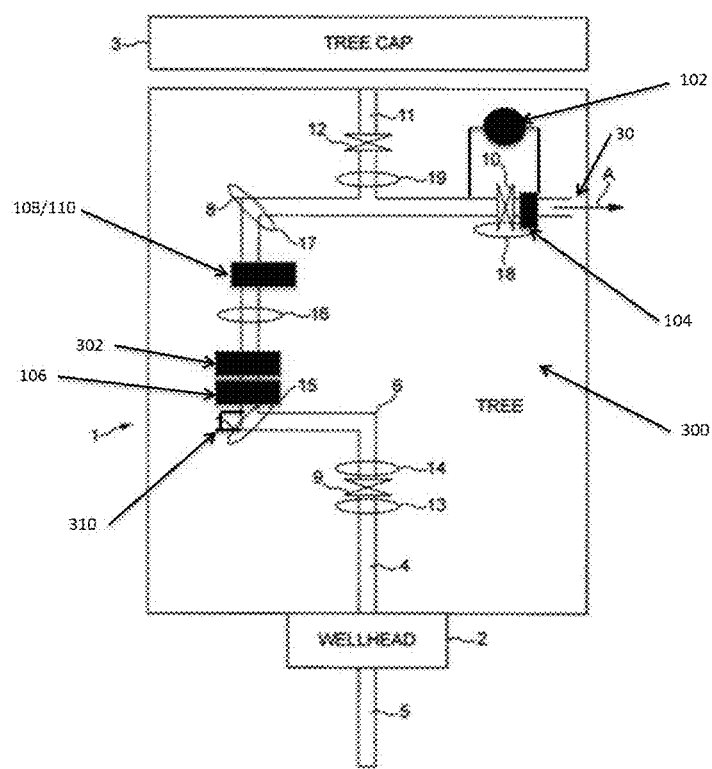
FIG. 5 is a schematic illustration of one example of a sensor arrangement for a christmas tree of a subsea hydrocarbon extraction facility incorporating aspects of the disclosed embodiments.

For a torsional sensor application, the first bulk density sensor 104 can be located in a blind T of the flow pipeline 4 in the christmas tree assembly 1. FIG. 5 shows one such example of a blind-T 310. Such a torsional sensor application can provide liquid density as denser fluid is pushed into a dead end portion of the Christmas tree. This torsional sensor application also enables erosion of the particular sensor to be avoided.

For a UT sensor application, the first bulk density sensor 104 can be located before or after a choke. Such a UT sensor typically works with single phase flow. Thus, the UT sensor needs to be in an area of high or low pressure to obtain liquid or gas instances, respectively. Referring to the example of FIG. 1, the first bulk density sensor 104 is positioned in a gas dominant flow region. In the location of the first bulk density sensor 104 shown in FIG. 1, the lower pressure will make complete a gas instance more likely. For a liquid flow instance, the position of the second bulk density sensor 106 would be preferred. The higher pressure before the choke 10 would make complete liquid path more likely and after the second sharp bend 7 and stratified gas at the top of the pipe 4 would be dispersed.

For a gamma sensor application, the bulk density sensor, such as the first bulk density sensor 104 is located after a choke. Alternatively, the bulk density sensor can be located in a vertical or upwards section of the christmas tree assembly 1 where flow is well mixed, such as the second bulk density sensor 106 shown in FIG. 1. A well mixed flow can typically be found after a sharp bend, such as the first, second and third sharp bends 6, 7, 8 shown in FIG. 1, or the blind T 310 shown in FIG. 5. In such an application, it is advantageous to dispose the gamma sensor in an area of well mixed flow where the different fluids and components are moving at substantially the same speed, and the fluid flow is axisymetric. This advantageously enables the measured density to be representative of the fluid flow in the flow pipeline 4 of the Christmas tree assembly 1.

The sensor assembly 100 for the Christmas tree 1 shown in FIG. 1 can also include a temperature transducer 108 and a pressure transducer 110. In one embodiment, the pressure and temperature sensor functions can be combined into a single instrument. The phase fractions and bulk density are temperature and pressure dependent. Thus, it is advantageous to know the temperature and pressure at which the bulk density measurement was made, which also allows the use of a pressure volume temperature (PVT) table and transferring to standardized conditions.

By measuring the temperature and pressure of the fluid flow through the fluid pipeline 4, the PVT look-up table can be used to estimate the gas volume fraction (GVF) at an assumed level of water cut. In combination with the differential pressure and bulk density, this will allow calculation of flow rates for the three phases of oil, water and gas.

In the example of FIG. 1, the temperature sensor 108 and pressure sensor 110 are generally located in a well-insulated region of the flow pipeline 4. In one embodiment, the temperature sensor 106 can be located in an area that is close to the density measurement area. For example, as is shown in FIG. 1, the temperature sensor 108 is located near the second bulk density sensor 106.

The location of the pressure sensor 110 can also be close to the density measurement area, or in an area that is away from any geometry change that would cause a pressure drop. In the example of FIG. 1, the pressure sensor 110 is located near the second bulk density sensor 106, in the region of the flow pipeline 4 between the second sharp bend 7 and the third sharp bend 8. This region can also be described as a substantially straight, upward or vertical region of the flow pipeline 4.

The example of FIG. 1 also has a second pressure sensor 18 located near the choke valve 10. In this example, the pressure sensor 18 is located near the first bulk density sensor 104.

Other typical measurements for which optimum positions shown in FIG. 1 can be identified on the christmas tree assembly 1 are described below.

For vibration and/or strain measurement, a sensor 13 can be located at or near the flow control valve 9. The flow control valve 9 is in an area which could cause vibration. Alternatively, the sensor 13 can be located at another position of maximum stress.

For particulate detection, such as sand detection, an acoustic sensor 15 I shown located at or near the second sharp bend 7 in the flow pipeline 4 to detect particle impact. The acoustic sensor 15 could also be located after the bends 6 and 8. As the acoustic sensor 15 is typically non-intrusive it can be fitted to the outside of the flow pipeline 4.

For ultrasound Doppler measurements for velocity, electrical impedance spectroscopy, microwave measurements or similar measurements, a sensor 16 can be located between the second sharp bend 7 and the third sharp bend 8 where there is a conditioned steady state flow. Using ultrasound for density or GVF would require a sensor at a blind T or an end of a long stretch of horizontal pipe.

For erosion measurement, a sensor 17 can be located at or near the third sharp bend 8, or where more significant erosion is expected. Alternative locations can include the first bend 6 or after the choke 10, not shown, to make a direct measurement.

Figure 3:
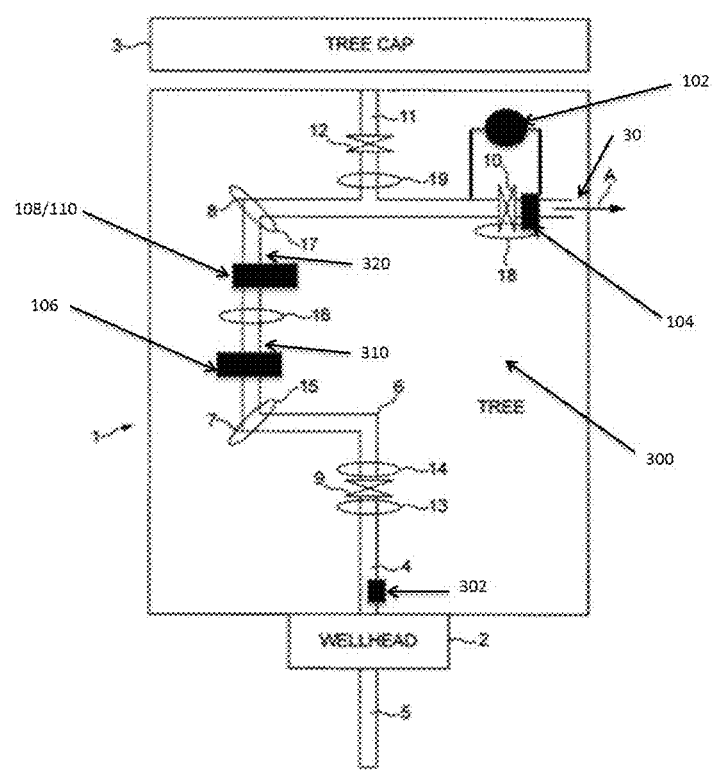
FIG. 3 is a schematic illustration of one example of a sensor arrangement for a christmas tree of a subsea hydrocarbon extraction facility incorporating aspects of the disclosed embodiments.

For pressure drop, a sensor 18 which measures pressure drop through a restriction or known change in geometry can be located across the choke valve 10 shown in FIG. 1, the differential pressure sensor 102 shown in FIG. 3, or across a dedicated flow restriction (venturi/v-cone . . . ), such as the position of the sensor 16 shown in FIG. 3.

For temperature measurement, a sensor 19 can be placed before the flow isolation valve 12 at or near a most isolated point from any interfering temperature.

Figure 2:
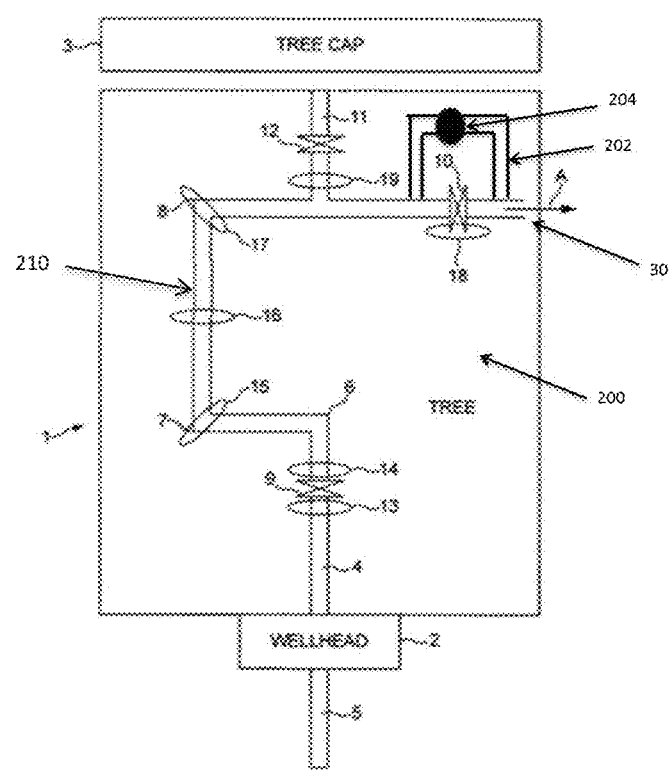
FIG. 2 is a schematic illustration of one example of a subsea christmas tree according to the disclosed embodiments.

FIG. 2 illustrates one embodiment of a christmas tree assembly 1 with a sensor assembly 200 incorporating aspect of the disclosed embodiments. In this example, the christmas tree assembly 1 includes a bypass line 202 in the flow pipeline 4. The bypass line 202 is disposed around the choke valve 10, between the third sharp bend 8 and the exit 30. A choke valve, such as the choke valve 10, can be used to ensure enough pressure drop to allow flow through the bypass line.

In one embodiment, a gas void fraction and/or water-cut sensor 204 is disposed in the bypass line 202. The gas void fraction sensor 204 is configured to measure the ratio of gas to liquid in the bypass line where it is representative of the gas to liquid ratio in the main flow. The water cut meter does the same but for water cut. Both of these measurements can be made more easily with smaller volumes of fluid (i.e. a small bypass line rather than the full pipe). While the aspects of the disclosed embodiments are generally described herein with respect to the gas void fraction sensor 204 being disposed in the bypass line 202, the aspects of the disclosed embodiments are not so limited. In one embodiment, the gas void fraction sensor 204 is disposed in any suitable portion of the flow pipe 4 where it can measure a ratio of gas to liquid in the main flow In one embodiment, the gas void fraction sensor 204 comprises one or more of an ultrasound level measurement sensor, a nuclear magnetic resonance (NMR) sensor or an electrical impedance spectroscopy sensor, a microwave sensor or a gamma densitometer. Where the gas void fraction sensor 204 is an ultrasound sensor, the sensor is located in an area of horizontal flow, such as a long horizontal section of the flow pipeline 4, making the measurement using the stratified nature of the flow. Generally, in a long horizontal pipe, liquid will sit at the bottom of the pipe and gas will flow along the top. The use of an ultrasound sensor as the gas void fraction sensor 204 enables measuring the liquid level in the flow pipeline 4, then uses the level information together with the known pipe geometry to determine the fraction of liquid and gas velocity.

In an application where the gas void fraction sensor 204 includes or comprises a NMR sensor, the NMR sensor can be located in a small diameter area of the flow pipeline 4. While the NMR sensor is located in a small diameter area, the power required to make the measurement is reduced to a manageable level and the fluid flow should be slow moving (due to increased pressure drop) for measurement purposes. For example, the fluid flow through the measurement area of the gas void fraction sensor 204, the bypass line 202 in FIG. 2, can be below approximately 6 meters/second.

Where the gas void fraction sensor 204 includes one or more of an electrical impedance spectroscopy (EIS) sensor, a microwave (MW) sensor or a gamma densitometer, the gas void fraction sensor 202 can be located in a vertically upward section of the fluid pipeline 4 after a sharp bend, such as location 210 referenced in FIG. 2, or after a choke, such as the choke 10. This is generally an area of well mixed flow, and is typically in a region of the flow pipeline area after a blind T, such as the blind T 310 of FIG. 5, or the choke 10. To obtain a representative GVF measurement, the volume of gas in the fluid pipeline at the point of measurement 4 needs to be representative of the general flow in the pipe. This implies avoiding measurement locations where liquid or gas may accumulate and is generally more easily obtained in vertically upward, well mixed flows. Furthermore, measurement in well mixed vertical flow regions allows the use of industry known correlations for the relative velocities of the different phases, such as the slip law.

FIGS. 3-6 illustrate embodiments of a Christmas tree assembly 1 including a sensor assembly 300 incorporating aspects of the disclosed embodiments. In these examples, the sensor assembly 300 includes one or more water cut meters 302. The water cut meter 302 can comprise one or more of a microwave near field probe (NFP), a microwave patch, an electrical impedance spectroscopy device, a nuclear magnetic resonance device or a capacitance device. The water cut meter 302 of the disclosed embodiments is configured to provide 3-phase flow measurements.

In the example of FIG. 3, the water cut meter 302 is disposed between the wellhead 2 and the flow control valve 9. In a well with gas dominant flow (wet gas), the measurement technique can rely on measuring the liquid that will tend to be on the pipe wall. In this embodiment, the water cut meter 302 comprises a microwave near field probe (NFP). The microwave NFP will be located close to a wall of the tree 100 in a high velocity flow area. The location will be after chemical injections but before any choke. This provides a liquid instance at the measurement device, and avoids waxing and scaling. In a liquid dominant well the measurement will work as there is also liquid at the wall of the pipe.

Figure 4:
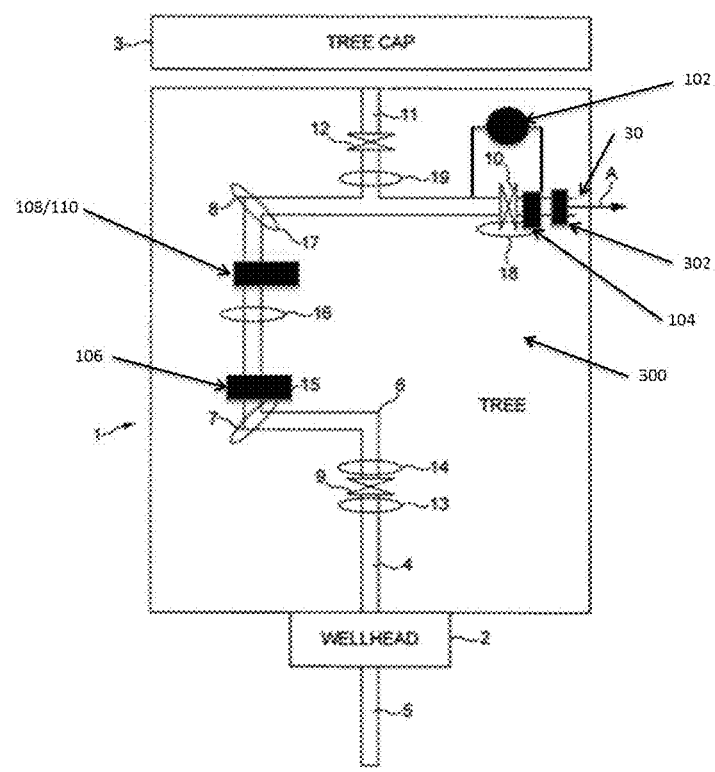
FIG. 4 is a schematic illustration of one example of a sensor arrangement for a christmas tree of a subsea hydrocarbon extraction facility incorporating aspects of the disclosed embodiments.

In the example of FIG. 4, the water cut meter 302 is located near the exit 30 of the flow pipeline 4. In a wet gas well the liquid droplets will be dispersed and the measurement technique measures the liquid toward the center of the pipe 4. In a liquid dominant well the measurement will work as there is also liquid in the centre of the pipe. In the example of FIG. 4, the water cut meter 302 is an infra-red (IR) absorption device.

In the example of FIG. 5, the water cut meter 302 is located in the portion of the flow pipeline 4 between the second sharp bend 7 and the third sharp bend 8. This is an area of likely to be liquid dominant flow due to higher pressure before the choke and the measurement technique measures the entire cross-section of the portion of the flow pipeline 4. In this example the measurement technique could be electrical impedance spectroscopy, transmission microwave, ultrasonic or other method that interrogates across the entire pipe. In this example, the christmas tree 1 includes a blind-T section 310. The well mixed nature of the fluid flow through the portion of the flow pipeline 4 after the blind-T section 310 improves the measurement.

Figure 6:
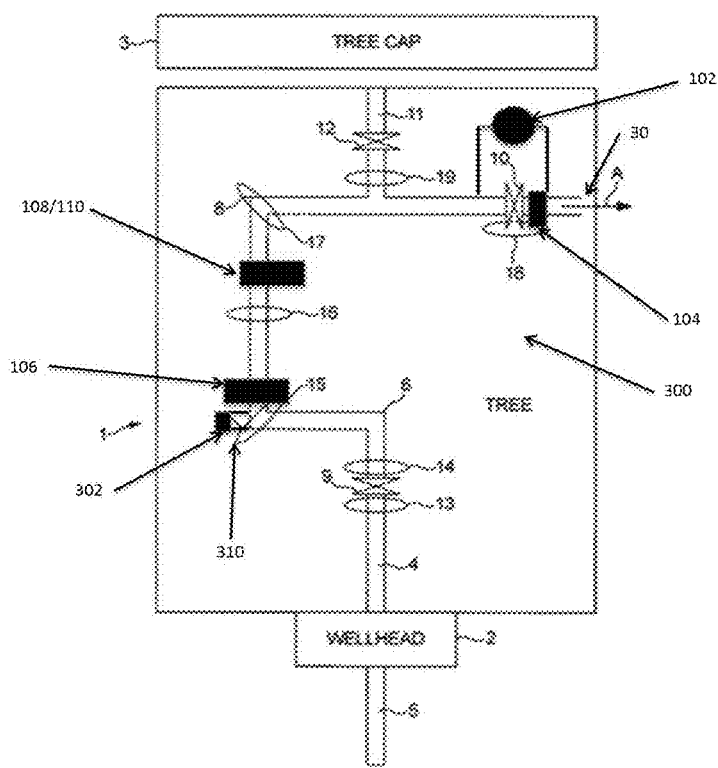
FIG. 6 is a schematic illustration of one example of a sensor arrangement for a christmas tree of a subsea hydrocarbon extraction facility incorporating aspects of the disclosed embodiments.

In the example of FIG. 6, the water cut meter 302 is disposed in the blind-T section 310 of the flow pipeline 4. The blind-T section 310 generally comprises a dead end portion 310 of the christmas tree 1. The length of the dead end portion should not be too long or too short. If the length of the dead end portion is too long, the fluid flow will stagnate. If the length of the dead end portion is too short, the fluid will not accumulate and the flow can erode the water cut meter 302. The measurement technique in this example relies on the local properties of accumulated fluid in the dead end portion of the blind-T section 310. In this example, the water cut meter 302 comprises a capacitance/torsional densitometer or gamma densitometer.

The microwave patch is typically located after a point of chemical injection, in an area of well mixed flow. Axial symmetry is needed for optimized results. The electrical impedance spectroscopy sensor is typically located after the choke in an upward flow section of the christmas tree 1. It is helpful to avoid short circuits around the circumference of the flow pipe 4. Locating the water cut meter 302 after the choke avoids short circuits.

In one embodiment, the sensor assembly 300 of FIG. 3 can also include a sensor to measure a velocity of one phase of the fluid flow through the christmas tree 1. For example, a first fluid flow sensor can be disposed at position 310 and a second fluid flow sensor disposed at position 320. By comparing the measurements at each position 310, 320, and the time between the measurements, the calculation of the velocity of the fluid flow can be made.

In this example, cross correlation of one or more of a microwave sensor, an electrical impedance sensor, a NMR sensor or an ultrasound Doppler can be used. In one embodiment, the microwave cross-correlation sensor, electrical impedance cross correlation sensor, or NMR cross-correlation sensor will typically be located in an area of fully developed fluid flow. This might be in a straight, upstream flow section. A continuous profile in the flow section is desired in order to avoid flow pattern changes.

The different sensors will be spaced a certain distance apart, specific to the velocity of the fluids. In a fast fluid flow environment, the different sensors will be further separated or spaced apart to increase the signal to noise ratio. In a slow fluid flow environment, the different sensors can be spaced closer together to allow accurate measurements without losing the patterns being correlated. This is pipe geometry dependent.

Electrical measurements taken by the microwave cross-correlation sensor and the electrical impedance cross-correlation sensor are sensitive to water. The electrical cross-correlation sensor can be used to either track the velocity of the water phase and estimate liquid velocity or track gas bubbles, giving gas velocity.

The ultrasound Doppler is disposed within the christmas tree 1 in an area of well mixed, fully developed fluid flow. This is typically an area as far as possible after a choke or blind T, such as the blind T 310 of FIG. 5. The ultrasound Doppler is configured to obtain a fluid flow velocity across the pipe that is axi-symetric.

The aspects of the disclosed embodiments offer a significantly more detailed and accurate method of measuring produced fluid properties compared to conventional methods. The aspects of the disclosed embodiments also offer increased functionality for a christmas tree assembly as compared to the conventional approach of integrating instruments attached to a christmas tree assembly as a co-located instrument package.

Thus, while there have been shown, described and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A christmas tree assembly for a subsea hydrocarbon extraction facility, the christmas tree assembly comprising:
   a flow pipeline; and
   a sensor assembly comprising a plurality of sensors configured to monitor a plurality of properties relating to hydrocarbon fluid flow through the flow pipeline, the sensor assembly comprising:
      a differential pressure sensor that is disposed across one or more of a choke, around a bend or restriction in the pipeline, or a dedicated flow restrictor integrated within the pipeline; and
      a bulk density sensor that is disposed in one or more of a blind T, before or after a choke, or in a vertical section of the flow pipeline.

2. The christmas tree assembly of claim 1, wherein the bulk density sensor is one or more of a torsional densitometer, an ultrasonic based density sensor, or a gamma based density sensor.

3. The christmas tree assembly of claim 1, wherein the bulk density sensor is disposed proximate to an output of a control valve in the flow pipeline.

4. The christmas tree assembly of claim 1, wherein the bulk density sensor is disposed in a straight portion of the flow pipeline between two sharp bends.

5. The christmas tree assembly of claim 1, wherein the sensor assembly further comprises a gas void fraction sensor disposed in a flow region of the flow pipeline.

6. The christmas tree assembly of claim 5, wherein the sensor assembly further comprises an ultrasound sensor and the flow region is a horizontal flow region.

7. The christmas tree assembly of claim 6, wherein the flow pipeline comprises a choke valve in a portion of the flow pipeline between a sharp bend and an exit of the flow pipeline, a bypass line disposed around the choke valve, and the gas void fraction sensor disposed in the bypass line.

8. The christmas tree assembly of claim 7, wherein the gas void fraction sensor comprises one or more of an ultrasound measurement device, a microwave measurement, or a nuclear magnetic resonance device.

9. The christmas tree assembly of claim 5, wherein the gas void fraction sensor is disposed in a vertical flow region of the flow pipeline.

10. The christmas tree assembly of claim 9, wherein the gas void fraction sensor comprises one or more of an electrical impedance spectroscopy device, a microwave device, or a gamma densitometer.

11. The christmas tree assembly of claim 1, wherein the sensor assembly further comprises a temperature sensor and a pressure sensor, the temperature sensor and the pressure sensor being disposed in proximity of the bulk density sensor.

12. The christmas tree assembly of claim 11, further comprising a water cut meter.

13. The christmas tree assembly of claim 12, wherein the water cut meter comprises a microwave NFP disposed in a high velocity area of the flow pipeline before a choke.

14. The christmas tree assembly of claim 12, wherein the water cut meter is an infrared absorption sensor configured to measure liquid phase toward a center of the flow pipeline.

15. The christmas tree assembly of claim 12, wherein the water cut meter is disposed in a blind T portion of the flow pipeline.

16. The christmas tree assembly of claim 12, wherein the sensor assembly further comprises a fluid velocity sensor disposed in a well mixed, fully developed flow region of the flow pipeline.

17. The christmas tree assembly of claim 16, wherein the sensor assembly further comprises one or more of a microwave cross correlation sensor, an electrical impedance cross correlation sensor, or an NMR cross correlation sensor disposed in a straight upstream section of the pipeline.

18. The christmas tree assembly of claim 16, wherein the sensor assembly further comprises an ultrasound Doppler sensor disposed after a choke or blind T in the flow pipeline.

19. The christmas tree assembly of claim 11, wherein the temperature sensor and the pressure sensor are disposed in an insulated region of the flow pipeline in proximity of the bulk density sensor.

20. The christmas tree assembly of claim 19, wherein the temperature sensor and the pressure sensor are disposed in a straight portion of the flow pipeline between two sharp bends.

21. The christmas tree assembly of claim 1, wherein the bulk density sensor is disposed in one of the blind T and the vertical section of the flow pipeline.

* * * * *